United States Patent [19]
Benoit et al.

[11] Patent Number: 5,919,453
[45] Date of Patent: Jul. 6, 1999

[54] MONOCLONAL ANTIBODIES AGAINST THE INTERFERON RECEPTOR, WITH NEUTRALIZING ACTIVITY AGAINST TYPE I INTERFERON

[75] Inventors: Patrick Benoit; Francois Meyer; Debborah Maguire, all of Paris; Ivan Plavec, Fresnes; Michael G. Tovey, Paris, all of France

[73] Assignee: Laboratoire European De Biotechnologie S.A., Paris, France

[21] Appl. No.: 08/307,588

[22] PCT Filed: Mar. 30, 1993

[86] PCT No.: PCT/EP93/00770

§ 371 Date: Dec. 5, 1994

§ 102(e) Date: Dec. 5, 1994

[87] PCT Pub. No.: WO93/20187

PCT Pub. Date: Oct. 14, 1993

[30] Foreign Application Priority Data

Mar. 31, 1992 [EP] European Pat. Off. .............. 92400902

[51] Int. Cl.$^6$ .................. A61K 39/395; C12P 21/08; C07K 16/00; C12N 5/06
[52] U.S. Cl. .................. 424/143.1; 424/133.1; 530/387.3; 530/387.9; 530/388.1; 530/388.22; 435/328; 435/331; 435/334
[58] Field of Search ............. 530/388.1, 388.23, 530/388.22, 387.3, 387.9; 435/7.2, 70.21, 172.2, 240.27, 325, 328, 334, 335, 331; 424/145.1, 143.1, 133.1

[56] References Cited

U.S. PATENT DOCUMENTS 5,516,515  5/1996  Vellucci et al. .................. 424/184.1

FOREIGN PATENT DOCUMENTS 0 369 877  5/1990  European Pat. Off. .
WO 91/05862  5/1991  WIPO .
9109967  7/1991  WIPO .

OTHER PUBLICATIONS

Riechmann et al., "Reshaping Human Antibodies for Therapy", vol. 332, Mar. 25, 1988, pp. 323–327.

Colamonichi et al., "Characterization of Three Monoclonal Antibodies that Recognize the Interferon $\alpha 2$ Receptor", Proc. Natl. Acad. Sci., vol. 87, Sep. 1990, pp. 7230–7234.

Langer et al., "Interferon Receptors", Immun. Today, vol. 9, No. 12, Dec. 1988, pp. 393–400.

Benoit et al., "A Monoclonal Antibody to Recombinant Human IFN–$\alpha$ Receptor Inhibits Biologic Activity of Several Species of Human IFN–$\alpha$, IFN–$\beta$, and IFN–$\Delta^1$", Journ. of Immun., vol. 150, No. 3, Feb. 1993, pp. 707–716.

Yonehara et al., "Monoclonal Anti–Idiotype Antibody for Anti–Human Interferon–$\alpha$ that complete with Interferon–$\alpha$ in Binding to Human Cell Surface and Inhibit the Interferon Action", Elsevier Sci. Publ. BV, (1986), pp. 167–171.

Larrick et al, Biotechniques, pp. 6–14, Jan.–Feb. 1984.

Waldmann, Thomas A., Science, 252:1657–1662, Jun. 1991.

Harris, W. J. et al, TIBTECH, 11:42–44, Feb. 1993.

*Primary Examiner*—Susan A. Loring
*Attorney, Agent, or Firm*—Foley & Lardner

[57] ABSTRACT

A monoclonal antibody directed against the human interferon type I receptor (IFN-R), which recognizes the extracellular domain of the human IFN-R and has neutralizing capacity against the biological properties of human type I-IFN. Diagnostic applications for the monoclonal antibody also are provided.

22 Claims, 9 Drawing Sheets

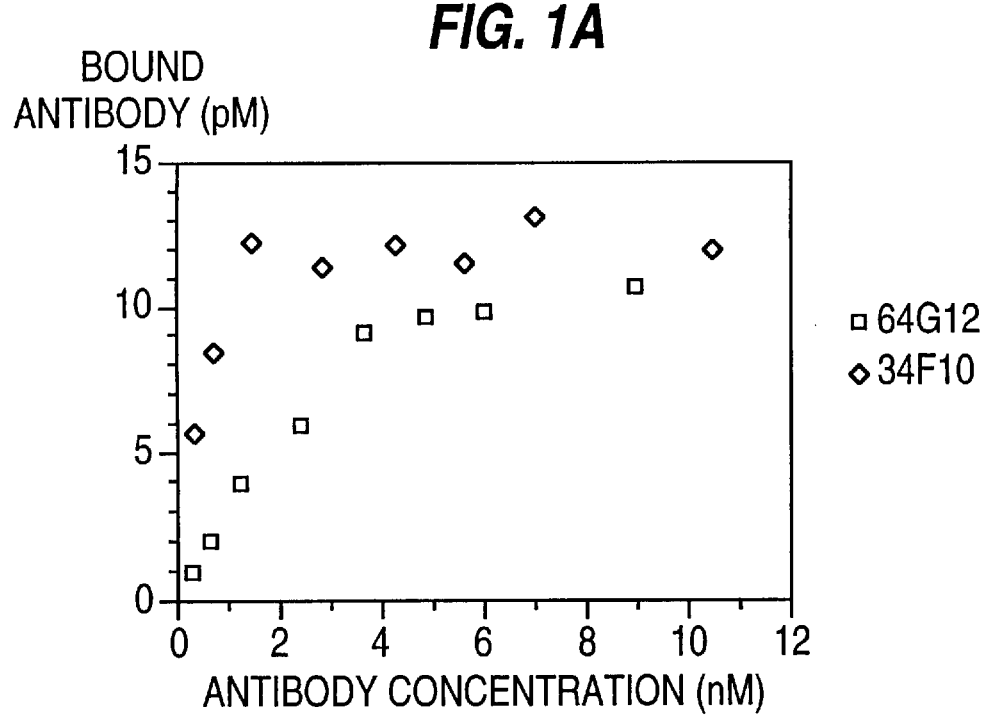
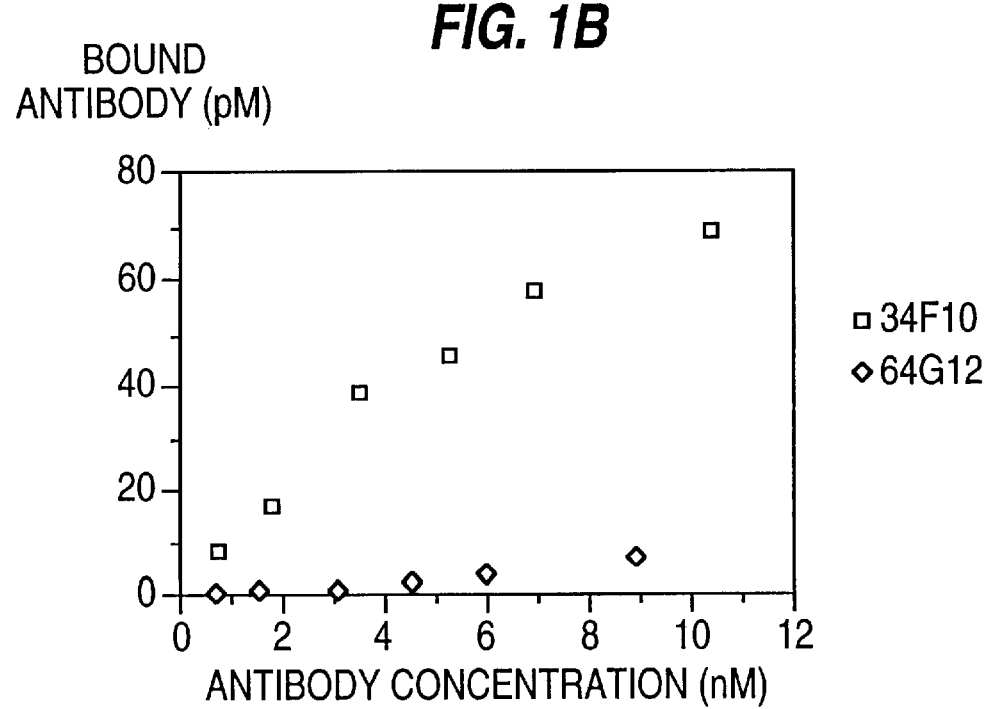

FIG. 2A

```
                                                          CTGCAGGGATCTGCGGGGCTCCCAG

ATG ATG GTC GTC CTC CTG GGC GCG ACG ACC CTA GTG CTC GCC GTG GGC CCA
Met Met Val Val Leu Leu Gly Ala Thr Thr Leu Val Leu Ala Val Gly Pro

TGG GTG TTG TCC GCA GCC GCA GGT GGA AAA AAT CTA AAA TCT CCT CAA AAA GTA
Trp Val Leu Ser Ala Ala Ala Gly Gly Lys Asn Leu Lys Ser Pro Gln Lys Val

GAG GTC GAC ATC ATA GAT GAC AAC TTT ATC CTG AGG TGG AAC AGG AGC GAT GAG
Glu Val Asp Ile Ile Asp Asp Asn Phe Ile Leu Arg Trp Asn Arg Ser Asp Glu

TCT GTC GGG AAT GTG ACT TTT TCA TTC GAT TAT CAA AAA ACT GGG ATG GAT AAT
Ser Val Gly Asn Val Thr Phe Ser Phe Asp Tyr Gln Lys Thr Gly Met Asp Asn

TGG ATA AAA TTG TCT GGG TGT CAG AAT ATT ACT AGT ACC AAA TGC AAC TTT TCT
Trp Ile Lys Leu Ser Gly Cys Gln Asn Ile Thr Ser Thr Lys Cys Asn Phe Ser

TCA CTC AAG CTG AAT GTT TAT GAA ATT AAA TTG CGT ATA AGA GCA GAA AAA
Ser Leu Lys Leu Asn Val Tyr Glu Ile Lys Leu Arg Ile Arg Ala Glu Lys

GAA AAC ACT TCT TCA TGG TAT GAG GTT GAC TCA TTT ACA CCA TTT CGC AAA GCT
Glu Asn Thr Ser Ser Trp Tyr Glu Val Asp Ser Phe Thr Pro Phe Arg Lys Ala

CAG ATT GGT CCT CCA GAA GTA CAT TTA GAA GAT AAG GCA ATA GTG ATA
Gln Ile Gly Pro Pro Glu Val His Leu Glu Asp Lys Ala Ile Val Ile
```

FIG. 2B

CAC ATC TCT CCT GGA ACA AAA GAT AGT GTT ATG TGG GCT TTG GAT GGT TTA AGC
His Ile Ser Pro Gly Thr Lys Asp Ser Val Met Trp Ala Leu Asp Gly Leu Ser

TTT ACA TAT AGC TTA CTT ATC TGG AAA AAC TCT TCA GGT GTA GAA GAA AGG ATT
Phe Thr Tyr Ser Leu Leu Ile Trp Lys Asn Ser Ser Gly Val Glu Glu Arg Ile

GAA AAT ATT TAT TCC AGA CAT AAA ATT TAT AAA CTC TCA CCA GAG ACT ACT TAT
Glu Asn Ile Tyr Ser Arg His Lys Ile Tyr Lys Leu Ser Pro Glu Thr Thr Tyr

TGT CTA AAA GTT AAA GCA GCA CTA CTT ACG TCA TGG AAA ATT GGT GTC TAT AGT
Cys Leu Lys Val Lys Ala Ala Leu Leu Thr Ser Trp Lys Ile Gly Val Tyr Ser

CCA GTA CAT TGT ATA AAG ACC ACA GTT GAA AAT GAA CTA CCT CCA CCA GAA AAT
Pro Val His Cys Ile Lys Thr Thr Val Glu Asn Glu Leu Pro Pro Pro Glu Asn

ATA GAA GTC AGT GTC CAA AAT CAG AAC TAT GTT CTT AAA TGG GAT TAT ACA TAT
Ile Glu Val Ser Val Gln Asn Gln Asn Tyr Val Leu Lys Trp Asp Tyr Thr Tyr

GCA AAC ATG ACC TTT CAA GTT CAG TGG CTC CAC GCC TTT TTA AAA AGG AAT CCT
Ala Asn Met Thr Phe Gln Val Gln Trp Leu His Ala Phe Leu Lys Arg Asn Pro

GGA AAC CAT TTG TAT AAA CAA ATA CCT GAC TGT GAA AAT GTC AAA ACT
Gly Asn His Leu Tyr Lys Gln Ile Pro Asp Cys Glu Asn Val Lys Thr

FIG. 2C

```
ACC CAG TGT GTC TTT CCT CAA AAC GTT TTC CAA AAA GGA ATT TAC CTT CTC CGC
Thr Gln Cys Val Phe Pro Gln Asn Val Phe Gln Lys Gly Ile Tyr Leu Leu Arg

GTA CAA GCA TCT GAT GGA AAT AAC ACA TCT TTT TGG TCT GAA GAG ATA AAG TTT
Val Gln Ala Ser Asp Gly Asn Asn Thr Ser Phe Trp Ser Glu Glu Ile Lys Phe

GAT ACT GAA ATA CAA GCT TTC CTA CTT CCT CCA GTC TTT AAC ATT AGA TCC CTT
Asp Thr Glu Ile Gln Ala Phe Leu Leu Pro Pro Val Phe Asn Ile Arg Ser Leu

AGT GAT TCA TTC CAT ATC TAT ATC GGT GCT CCA AAA CAG TCT GGA AAC ACG CCT
Ser Asp Ser Phe His Ile Tyr Ile Gly Ala Pro Lys Gln Ser Gly Asn Thr Pro

GTG ATC CAG GAT TAT CCA CTG ATT ATT TAT GAA ATT TTT TGG GAA AAC ACT TCA
Val Ile Gln Asp Tyr Pro Leu Ile Ile Tyr Glu Ile Phe Trp Glu Asn Thr Ser

AAT GCT GAG AGA AAA ATT ATC GAG AAA AAA ACT GAT GTT ACA GTT CCT AAT TTG
Asn Ala Glu Arg Lys Ile Ile Glu Lys Lys Thr Asp Val Thr Val Pro Asn Leu
```

FIG. 2D

```
AAA CCA CTG ACT GTA TAT TGT GTG AAA GCC AGA GCA CAC ACC ATG GAT GAA AAG
Lys Pro Leu Thr Val Tyr Cys Val Lys Ala Arg Ala His Thr Met Asp Glu Lys

CTG AAT AAA AGC AGT GTT TTT AGT GAC GCT GTA TGT GAG AAA ACA AAA CCA GGA
Leu Asn Lys Ser Ser Val Phe Ser Asp Ala Val Cys Glu Lys Thr Lys Pro Gly

AAT ACC TCT AAA TGA GGT ACC
Asn Thr Ser Lys
```

FIG. 3A

```
                                                    CTGCAGGATCTGCGGGCTCCAG

ATG ATG GTC GTC CTC CTG GGC GCG ACC CTA GTG CTC GTC GCC GTG GGC CCA
Met Met Val Val Leu Leu Gly Ala Thr Leu Val Leu Val Ala Val Gly Pro

TGG GTG TTG TCC GCA GCC GCA GGT GGA AAA AAT CTA AAA TCT CCT CAA AAA GTA
Trp Val Leu Ser Ala Ala Ala Gly Gly Lys Asn Leu Lys Ser Pro Gln Lys Val

GAG GTC GAC ATC ATA GAT GAC AAC TTT ATC CTG AGG TGG AAC AGG AGC GAT GAG
Glu Val Asp Ile Ile Asp Asp Asn Phe Ile Leu Arg Trp Asn Arg Ser Asp Glu

TCT GTC GGG AAT GTG ACT TTT TCA TTC GAT TAT CAA AAA ACT GGG ATG GAT AAT
Ser Val Gly Asn Val Thr Phe Ser Phe Asp Tyr Gln Lys Thr Gly Met Asp Asn

TGG ATA AAA TTG TCT GGG TGT CAG AAT ATT ACT AGT ACC AAA TGC AAC TTT TCT
Trp Ile Lys Leu Ser Gly Cys Gln Asn Ile Thr Ser Thr Lys Cys Asn Phe Ser

TCA CTC AAG CTG AAT GTT TAT GAA ATT AAA GAA TTG CGT ATA AGA GCA GAA AAA
Ser Leu Lys Leu Asn Val Tyr Glu Ile Lys Leu Arg Ile Arg Ala Glu Lys

GAA AAC ACT TCT TCA TGG TAT GAG GTT GAC TCA TTT ACA CCA TTT CGC AAA GCT
Glu Asn Thr Ser Ser Trp Tyr Glu Val Asp Ser Phe Thr Pro Phe Arg Lys Ala

CAG ATT GGT CCT CCA GAA GTA CAT TTA GAA GCT GAA GAT AAG CTG ATA GTG ATA
Gln Ile Gly Pro Pro Glu Val His Leu Glu Ala Glu Asp Lys Leu Val Ile Ile
```

FIG. 3B

```
CAC ATC TCT CCT GGA ACA AAA GAT AGT GTT ATG TGG GCT TTG GAT GGT TTA AGC
His Ile Ser Pro Gly Thr Lys Asp Ser Val Met Trp Ala Leu Asp Gly Leu Ser

TTT ACA TAT AGC TTA CTT ATC TGG AAA AAC TCT TCA GGT GTA GAA GAA AGG ATT
Phe Thr Tyr Ser Leu Leu Ile Trp Lys Asn Ser Ser Gly Val Glu Glu Arg Ile

GAA AAT ATT TAT TCC AGA CAT AAA ATT TAT AAA CTC TCA CCA GAG ACT ACT TAT
Glu Asn Ile Tyr Ser Arg His Lys Ile Tyr Lys Leu Ser Pro Glu Thr Thr Tyr

TGT CTA AAA GTT AAA GCA GCA CTA CTT ACG TCA TGG AAA ATT GGT GTC TAT AGT
Cys Leu Lys Val Lys Ala Ala Leu Leu Thr Ser Trp Lys Ile Gly Val Tyr Ser

CCA GTA CAT TGT ATA AAG ACC ACA GTT GAA AAT GAA CTA CCT CCA GAA AAT
Pro Val His Cys Ile Lys Thr Thr Val Glu Asn Glu Leu Pro Pro Glu Asn

ATA GAA GTC AGT GTC CAA AAT CAG AAC TAT GTT CTT TGG GAT TAT ACA TAT
Ile Glu Val Ser Val Gln Asn Gln Asn Tyr Val Leu Trp Asp Tyr Thr Tyr

GCA AAC ATG ACC TTT CAA GTT CAG TGG CTC CAC GCC TTT AAA AGG AAT CCT
Ala Asn Met Thr Phe Gln Val Gln Trp Leu His Ala Phe Lys Arg Asn Pro

GGA AAC CAT TTG TAT AAA TGG AAA CAA ATA CCT GAC TGT GAA AAT GTC AAA ACT
Gly Asn His Leu Tyr Lys Trp Lys Gln Ile Pro Asp Cys Glu Asn Val Lys Thr
```

FIG. 3C

```
ACC CAG TGT GTC TTT CCT CAA AAC GTT TTC CAA AAA GGA ATT TAC CTT CGC
Thr Gln Cys Val Phe Pro Gln Asn Val Phe Gln Lys Gly Ile Tyr Leu Arg

GTA CAA GCA TCT GAT GGA AAT AAC ACA TCT TTT TGG TCT GAA GAG ATA AAG TTT
Val Gln Ala Ser Asp Gly Asn Asn Thr Ser Phe Trp Ser Glu Glu Ile Lys Phe

GAT ACT GAA ATA CAA GCT TTC CTA CTT CCT CCA GTC TTT AAC ATT AGA TCC CTT
Asp Thr Glu Ile Gln Ala Phe Leu Leu Pro Pro Val Phe Asn Ile Arg Ser Leu

AGT GAT TCA TTC CAT ATC TAT ATC GGT GCT CCA AAA CAC TCT GGA AAC ACG CCT
Ser Asp Ser Phe His Ile Tyr Ile Gly Ala Pro Lys His Ser Gly Asn Thr Pro

GTC ATC CAG GAT TAT CCA CTG ATT TAT GAA ATT ATT TTT TGG GAA AAC ACT TCA
Val Ile Gln Asp Tyr Pro Leu Ile Tyr Glu Ile Ile Phe Trp Glu Asn Thr Ser

AAT GCT GAG AGA AAA ATT ATC GAG AAA AAA ACT GAT GTT ACA GCC CCT AAT TTG
Asn Ala Glu Arg Lys Ile Ile Glu Lys Lys Thr Asp Val Thr Ala Pro Asn Leu

AAA CCA CTG ACT GTA TAT TGT GTG AAA GCC AGA GCA CAC ACC ATG GAT GAA AAG
Lys Pro Leu Thr Val Tyr Cys Val Lys Ala Arg Ala His Thr Met Asp Glu Lys

CTG AAT AAA AGC AGT GTT TTT AGT GAC GCT GTA TGT GAG AAA ACA AAA CCA GGA
Leu Asn Lys Ser Ser Val Phe Ser Asp Ala Val Cys Glu Lys Thr Lys Pro Gly
```

FIG. 3D

```
AAT ACC TCT AAA ATT TGG CTT ATA GTT GGA ATT TGT ATT GCA TTA TTT GCT CTC
Asn Thr Ser Lys Ile Trp Leu Ile Val Gly Ile Cys Ile Ala Leu Phe Ala Leu

CCG TTT GTC ATT TAT GCT GCG AAA GTC TTC TTG AGA TGC ATC AAT TAT GTC TTC
Pro Phe Val Ile Tyr Ala Ala Lys Val Phe Leu Arg Cys Ile Asn Tyr Val Phe

TTT CCA TCA CTT AAA CCT TCT TCC AGT ATA GAT GAG TAT TTC TCT GAA CAG CCA
Phe Pro Ser Leu Lys Pro Ser Ser Ser Ile Asp Glu Tyr Phe Ser Glu Gln Pro

TTG AAG AAT CTT CTG TCA ACT TCT GAG GAA CAA ATC GAA AAA TGT TTC ATA
Leu Lys Asn Leu Leu Ser Thr Ser Glu Glu Gln Ile Glu Lys Cys Phe Ile

ATT GAA AAT ATA AGC ACA ATT GCT ACA GTA GAA GAA ACT AAT CAA ACT GAT GAA
Ile Glu Asn Ile Ser Thr Ile Ala Thr Val Glu Glu Thr Asn Gln Thr Asp Glu

GAT CAT AAA AAA TAC AGT TCC CAA ACT AGC CAA GAT TCA GGA AAT TAT TCT AAT
Asp His Lys Lys Tyr Ser Ser Gln Thr Ser Gln Asp Ser Gly Asn Tyr Ser Asn

GAA GAT GAA AGC GAA AGT AAA ACA AGT GAA GAA CTA CAG CAG GAC TTT GTA TGA
Glu Asp Glu Ser Glu Ser Lys Thr Ser Glu Glu Leu Gln Gln Asp Phe Val

CCAGAAATGAACTGTGTCAAGTATAAGGTTTTTCAGCAGGAGTTACACTGGTACC
```

MONOCLONAL ANTIBODIES AGAINST THE INTERFERON RECEPTOR, WITH NEUTRALIZING ACTIVITY AGAINST TYPE I INTERFERON

This application is the National Stage of International Application PCT/EP93/00770, filed Mar. 30, 1993.

The interferons (IFN) constitute a group of secreted proteins which exhibit a wide range of biological activities and are characterized by their capacity to induce an antiviral state in vertebrate cells (I. Gresser and M. G. Tovey Biochem Biophys. Acta 516:231, 1978). There are three antigenic classes of IFN: alpha ($\alpha$), beta ($\beta$) and gamma. IFN$\alpha$ and IFN$\beta$ together are known as the type I interferon.

Natural type I human interferon comprises 12 or more closely related proteins encoded by distinct genes with a high degree of structural homology (Weissmann and Weber, Prog. Nucl. Acid. Res. Mol. Biol. 33:251, 1986).

The human IFN$\alpha$ locus comprises two subfamilies. The first subfamily consists of 14 non allelic genes and 4 pseudogenes having at least 80% homology. The second subfamily, $\alpha$II or omega ($\omega$), contains 5 pseudogenes and 1 functional gene which exhibits 70% homology with the IFN$\alpha$ genes (Weissmann and Weber 1986).

The subtypes of IFN$\alpha$ have different specific activities but they possess the same biological spectrum (Streuli et al. PNAS-USA 78:2848, 1981) and have the same cellular receptor (Agnet M. et al. in "Interferon 5" Ed. I. Gresser p. 1–22, Academic Press, London 1983).

The interferon $\beta$ (IFN$\beta$) is encoded by a single gene which has approximately 50% homology with the IFN$\alpha$ genes.

The interferon a subtypes and interferon $\beta$ bind to the same receptor on the cell surface.

The interferon gamma (IFN gamma) is also encoded by a single copy, which has little homology with the IFN$\alpha$ and IFN$\beta$ genes. The receptor for IFN gamma is distinct from the receptor of the $\alpha$ and $\beta$ interferons.

For the purpose of the present invention the receptor of $\alpha$ and $\beta$ classes of IFN will be designated IFN-R. This represents natural type I receptor. The group of proteins forming natural interferon $\alpha$ will be designated IFN$\alpha$, and type I-IFN will represent both natural IFN$\alpha$, IFN$\omega$, and IFN$\beta$.

Despite the fact that interferon is a potent antiviral agent, there is considerable evidence to suggest, that many of the characteristic symptoms of acute virus diseases such as upper respiratory tract infections are caused by an overproduction of interferon alpha. Furthermore, IFN alpha has been shown to contribute to the pathogenesis of certain chronic virus infections in experimental animals and the available evidence suggests that this is also the case for certain human chronic virus diseases such as those due to measles virus.

The interferons $\alpha$ are also potent immunoregulatory molecules which stimulate polyclonal B-cell activation, enhance NK cell cytotoxicity, inhibit T-cell functions, and modulate the expression of the major histocompatibility complex (MHC) class 1 antigens, all of which are implicated in the induction of autoimmunity and in graft rejection. The abnormal production of interferon $\alpha$ is associated with a number of autoimmune diseases and inflammatory disorders including systemic lupus erythematosus (SLE), type I diabetes, psoriasis, rheumatoid arthritis, multiple sclerosis, Behcet's disease, aplastic anemia, the acquired immunodeficiency syndrome (AIDS) and severe combined immunodeficiency disease. The presence of interferon $\alpha$ in the serum of patients with systemic lupus is correlated with both the clinical and humoral signs of increased disease activity. The production of interferon $\alpha$ in HIV positive subjects is also highly predictive of disease evolution.

Administration of interferon $\alpha$ has been reported to exacerbate underlying disease in patients with psoriasis and multiple sclerosis and to induce a SLE like syndrome in patients without a previous history of autoimmune disease. Interferon $\alpha$ has also been shown to induce glomerulonephritis in normal mice and to accelerate the outset of the spontaneous autoimmune disease of NZB/W mice.

Interferon $\alpha$ is also produced during the course of graft-versus-host disease (GVHD) in parallel with the enhanced NK cell activity characteristic of systemic GVDH. Interferon $\alpha$ is the principal modulator of NK cell cytotoxicity and administration of interferon $\alpha$ has been shown to enhance the intestinal consequences of GVDH in normal mice.

The object of the present invention is to provide new antagonists against the biological activities of the human type I-IFN. These antagonists could be used for therapeutical, including prophylaxis purposes, in cases where the type I-IFN (IFN $\alpha/\beta$) is abnormaly produced and when this abnormal production is associated with pathological symptoms. Such antagonists could also be used for the diagnosis of various diseases or for the study of the evolution of such diseases.

In order to define such antagonists, the inventors have taken into account the fact that the human natural type I-IFN is in fact constituted of a mixture of interferons (subspecies) and the fact that the composition of this association of different subtypes of interferons varies both quantitatively and qualitatively.

Some natural interferons, such as the ones secreted by Namalwa cells (Namalwa interferon) or leukocyte (leucocyte interferon) have been studied in detail (N. B. Finter and K. H. Fautes, Interferon 2, 1980, p. 65–79 I. Gresser Editor Academic Press; K. Cantell et al, Interferon 1, 1979 p. 2–25, I. Gresser Editor Academic Press) and were used by the inventors to define natural type I interferons.

In some pathological cases, like AIDS, interferons having some special properties have been described (O. T. Preble et al, Annals of New-York Academy of Sciences p. 65–75). This interferon involved in pathological cases like AIDS nevertheless binds to the same receptor, as described above.

One object of the present invention is to provide an antagonist of the type I-IFN, which would be able to inhibit or neutralize, to a determined extent, the biological properties of the human type I-IFN, that is to say, to neutralize in vivo a mixture of $\alpha$, $\beta$, $\omega$ subspecies.

Accordingly the inventors have defined antibodies, especially monoclonal antibodies, which have the property of being antagonists to the type I-IFN. These antibodies are directed against the human type I-IFN receptor.

The invention thus also concerns the use of the monoclonal antibodies for the preparation of pharmaceutical compositions, useful for the treatment of symptoms associated with the abnormal production of type I-IFN. These monoclonal antibodies are also appropriate for the preparation of diagnosis reagents.

A monoclonal antibody according to the present invention is directed against the human type I-interferon receptor (IFN-R) and is characterized by the following properties:

it recognizes the extracellular domain of the human IFN-R, and it has a neutralizing capacity against the biological properties of the human type I-IFN.

The ability to neutralize the biological properties of type I-IFN can be estimated as a function of the capacity of the monoclonal antibody to neutralize the antiviral activity of the type I-IFN. Such a test is relevant in order to determine whether the antibody assayed is included within the scope of the invention, although it is clear that the biological properties of type I-IFN are not limited to its antiviral properties. Detailed procedures are given in the examples in order to enable to perform such a test of the antiviral activity. The cells tested can advantageously be Daudi-cells, which affinity for the type I-IFN is well known. The main steps of such a test would consist in:

incubating a determined concentration of human cells responsive to human type I-IFN, with human type I-IFN in the presence of a determined concentration of monoclonal antibodies to be assayed, for a time sufficient to allow the formation of a complex between the monoclonal antibodies and the IFN-R of the human cells and/or between the type I-IFN and the IFN-R of the human cells;

infecting the incubated cells with a determined virus, in a determined concentration, washing the cells, resuspending the cells in culture medium, incubating for a time sufficient to allow virus replication;

lysing the cells;

measuring the virus replication, or measuring the inhibition of the cytopathic effect.

The ability of the monoclonal antibodies of the invention to neutralize the biological properties of the human type I-IFN can be modulated as a function of the dose of antibodies used. Accordingly a 100% inhibition of the biological properties, or a partial inhibition can be obtained.

According to another embodiment of the present invention, the monoclonal antibodies directed against the human type I-IFN receptor, are further characterized by the fact that they are capable of inhibiting the binding of a human type I-IFN, to the human IFN-R.

A monoclonal antibody having the capacity to recognize the extracellar domain of the human IFN-R and capable of inhibiting the binding of the human type I-IFN to its receptor, can be selected by the following steps:

preincubating a determined concentration of purified monoclonal antibodies or a hybridoma culture supernatant containing monoclonal antibodies to be assayed, with human cells capable of harboring IFN-R;

adding labelled human type I-IFN, in a determined concentration, to the above preincubated medium;

incubating the medium containing the human cells, the monoclonal antibodies and the labelled type I-IFN for a time sufficient to allow an equilibrium to occur, between the monoclonal antibodies on the one hand and the type I-IFN on the other hand, with the cellular IFN-R;

washing the cells;

determining the formation of a binding complex between the human cells and the labelled type I-IFN by counting the amount of attached labelled type I-IFN.

Some of the monoclonal antibodies of the invention, have also the capacity to neutralize the antiproliferative properties of the human type I-IFN. This property can also be assayed on Daudi cells, by performing the following steps:

allowing cells to grow in presence of human type IFN and determined concentration of mAb;

counting the cells in order to detect an inhibition of the antiproliferative effect of the human type I-IFN.

One property of a monocolonal antibody according to the invention resides in its capacity to recognize the extracellular domain of the human IFN receptor. This property of the monoclonal antibody can be assayed on human cells bearing the natural human receptor but also on the extracellular domain of a recombinant IFN-R such as expressed in a procaryotic cell, for instance in *E.coli* or a recombinant IFN-R such as expressed in a eucaryotic cell such as mamalian cell for instance a CHO-cell. This receptor can indeed present different properties, depending on the fact that it is produced in a procaryotic or eucaryotic cell and accordingly depending on the fact that the post-translational maturation occurred or not. The inventors interestingly showed that relevant assays, to evaluate the capacity of a monoclonal antibody according to the invention i.e. to recognize the cellular IFN-R, can be performed on a recombinant receptor expressed in mamalian cells. As a matter of fact, such recombinant receptor has the same properties as the cellular receptor, as far as its recognizing activity is concerned.

Monoclonal antibodies of the invention can be obtained against various forms of the receptor, including the complete receptor, a particular domain or a peptide characteristic of the aminoacid sequence of the receptor represented in FIG. 3 (SEQ ID NOS: 3–4).

Monoclonal antibodies of the invention can for example be prepared against the soluble form of the receptor. A hydrosoluble polypeptide corresponding to the soluble form of the INF-R is described on FIG. 2 (SEQ ID NOS: 1–2). According to the present invention, a soluble form of the IFN-R corresponds to a peptide or a polypeptide, capable of circulating in the body.

Other monoclonal antibodies according to the invention can also be prepared against a peptide comprised in the extracellular domain of the receptor as described on FIG. 2 (SEQ ID NOS: 1–2). An advantageous peptide corresponds for instance to the aminoacid sequence comprised between aminoacid 1 and aminoacid 229 of SEQ ID NO: 1 or 2. According to another embodiment of the invention, the antibodies can be prepared against a polypeptide modified by substitution of one or more amino acids, provided that antibodies directed against the non modified extracellular domain of the IFN-R, recognize the modified polypeptide or peptide.

Preferred monoclonal antibodies according to the invention are those which are of the IgG1 type.

Among the antibodies of the invention, an antibody which has the capacity of inhibiting the binding of the type I-IFN to its receptor is preferably characterized in that it inhibits the in vitro binding of human type IFN, to the human cellular IFN-R when it is co-incubated with cells harboring the hu-IFN-R, at a concentration of antibodies equal or inferior to 100 μg/ml, preferably equal or inferior to 50 μg/ml, advantageously inferior to 20 μg/ml, more preferably in the range of approximately 0.5 to 2 μg/ml.

The inventors have shown that the high affinity binding capacity of a monoclonal antibody is not sufficient to ensure that this antibody will be able to inhibit the binding activity of the human type I-IFN to the IFN-R. Nevertheless the high affinity binding capacity of the monoclonal antibody is necessary to investigate further the ability of the antibody to inhibit the binding of the type I-IFN to its cellular receptor.

Another monoclonal antibody is characterized in that it neutralizes in vitro the antiproliferative activity of human type I-IFN, on cells highly responsive to this human type I-IFN, for instance Daudi cells at a concentration in a range of 1 to 10 μg/ml.

According to another embodiment a monoclonal antibody is also characterized in that it neutralizes in vitro the antiproliferative activity of human type IFN, on cells poorly responsive to this human IFN, for instance Ly28 cells, at a concentration in a range of 50 to 100 μg/ml.

A particular group of monoclonal antibodies according to the invention is characterized in that it neutralizes the antiviral activity of the human type I-IFN, on cells highly responsive to this human type I-IFN, for instance Daudi cells at a concentration in a range of 1 to 50 μg/ml, preferably 1 to 20 μg/ml, for a concentration of type I-IFN in the range of 1 to 1000 units with reference to the international standard MRC 69/19.

Advantageously, the monoclonal antibody according to the invention is such that these antibodies do not bind to the human receptor for IFN gamma.

One particular antibody satisfying the requirements of the invention, is such as it is directed against an epitope on the amino-acid sequence comprised between amino-acid 27 and amino-acid 427 of the extracellular domain of the human IFN-R as represented on FIG. 2 (SEQ ID NOS: 1–2).

One particularly interesting monoclonal antibody according to the invention is the antibody designated 64G12 under n° 92022605 which has been deposited at the ECACC (European Collection of Animal Cell Cultures Porton Down Salisbury, Wiltshire SP4 056, United Kingdom) on Feb. 26, 1992.

These antibodies may be prepared by conventional methods involving the preparation of hybridoma cells by the fusion of myeloma cells and spleen cells of an animal immunized beforehand with the peptide antigen, on the conditions such that the antigen against which the antibodies are formed is constituted by the extracellular domain of IFN-R or any polypeptide or peptide of this domain.

The hybridomas are constructed according to the protocole of Kohler and Milstein (Nature, 1974, 256: 495–497). For example the hybridomas are derived from the fusion of the spleen cells above described with NS1 mouse (BalbC) HGPRT⁻ as myeloma cell.

A second procedure for the production of monoclonal antibodies according to the invention, consists in carrying out the fusion between B-cells of blood immortalized with the Epstein/Barr virus and human B lymphocytes placed beforehand in contact with the extracellular domain or a fragment thereof of the IFN-R, against which it is decided to form monoclonal antibodies. B-cells placed in contact beforehand with the extracellular domain of IFN-R or fragment thereof against which it is decided to form monoclonal antibodies, may be obtained by in vitro culture contacted with the antigens, the recovery of the B-cells coated with these antigens being preceded by one or several cycles of stimulation.

The invention thus concerns human antibodies as obtained by carrying out the above procedure, having the above defined properties.

The invention also aims at providing a monoclonal antibody characterized in that the variable or complementary determining regions of its heavy and/or light chains are grafted on the framework and/or constant regions of a human antibody.

The invention further provides a composition having antagonist properties for the biological properties of the human type I-IFN, characterized in that it comprises monoclonal antibodies as defined above.

Accordingly the invention provides a pharmaceutical composition characterized in that it comprises monoclonal antibodies as defined above, together with an appropriate pharmaceutical vehicle.

The invention also concerns the use of a monoclonal antibody as defined above, for the manufacture of a drug for the treatment or profilaxis of a pathological state or symptoms associated with overproduction of type-I-IFN.

According to a first example, the antibodies can be used in a pharmaceutical composition, for the treatment of allograft rejection.

According to another example, antibodies of the invention are used as active principle in a pharmaceutical composition for the treatment of autoimmune and inflammatory diseases. Such diseases include systemic lupus erythematosus, type 1 diabetes, psoriasis, rheumatoid arthritis, multiple sclerosis, Behcet's disease, asplatic anemia, acquired immunodeficiency syndrome (AIDS), and severe combined immunodeficiency disease.

Treatment of acute virus diseases can also be performed with the antibodies of the invention. As example upper respiratory tract infections, chronic virus infections such as those due to measles virus, can be performed.

The antibodies of the invention can also be used for the in vitro diagnosis of the presence of the human type I-IFN receptor or cells.

Further details and additional information will arise from the description from the description of the examples and from the figures.

FIGURES

FIG. 1: binding of $^{125}$I-labelled monoclonal antibodies 34F10 and 64G12 to:

A: Daudi cells

B: Ly28 cells

Briefly, $10^6$ cells were incubated for 2 hours at 4° C. in presence of different amounts of the labelled antibodies diluted in RPMI medium containing 10% fetal calf serum (FCS). The cells were then washed 4 times in RPMI-1% FCS and counted for bound radioactivity. Nonspecific binding was mesured by incubation with a 100 fold exces of cold antibodies and substracted from total counts.

FIG. 2: nucleotide and corresponding amino-acid sequence (SEQ ID NOS: 1–2) of the extracellular domain of the human IFN-R The monoclonal antibodies were produced against recombinant soluble forms of the human interferon alpha-beta receptor (IFN-R) synthetized in either procaryotic cells (*E.coli*) or a mammalian cell system (Cos cell). These soluble forms were based on the DNA sequence described in FIG. 2.

FIG. 3: nucleotide and corresponding amino-acid sequence (SEQ ID NOS: 3–4) of the human IFN-R.

EXAMPLES

Example 1

Synthesis of the Soluble Receptors Synthesis in *E.coli*

A fragment of DNA containing the sequence coding for the extracellular domain (amino acids 27 to 427) of the human INF-R (FIG. 2; SEQ ID NOS: 1–2), in which an extra-sequence coding for 5 histidyl residues was introduced just before the termination codon, was cloned in the expression vectors pKK233-2. This fragment was produced by the Polymerase Chain Reaction (PCR) and the resulting plasmids were sequenced to confirm both in-frame insertion with the Shine-Dalgarno sequence and the appropriate sequence coding for the receptor.

The poly-histidyl tail introduced into the recombinant protein enables it to be purified rapidly by affinity chromatography on a chelated nickel support (NTA column) as described previously (Hochuli E. et al, Bio/technology, 1988, 1321–1325).

The plasmid was introduced into the *E.coli* strain, JM105, and protein synthesis induced by addition of IPTG to the culture medium (pKK233-2, tac promoter).

Proteins were extracted from the bacterial pellet and the soluble receptor purified to homogeneity by affinity chromatography as described hereafter. This procedure yieled a protein that migrates as 2 bands around 50 kDa under reducing conditions and three bands under non-reducing conditions. The maximum concentration of the protein obtained by different procedures was approximately 20 µg/ml.

The N-terminal sequence of the two proteins detected by gel electrophoresis has shown that both proteins are the expected fragment of the receptor.

Synthesis and Purification of an Unglycosylated Soluble Receptor:

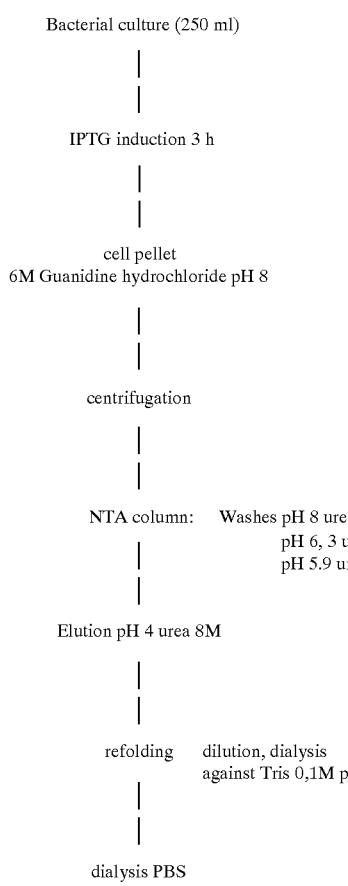

Using the same PCR approach, we also constructed an expression vector coding for the IFN-R amino acid sequence 1–427, with an additional 5-histidyl residues at the C-terminus, inserted in expression vector pXMT-3. The exact nucleotide sequence of the insert was also confirmed.

The resulting plasmid was introduced by electroporation into Cos7 cells for transient expression and the recombinant protein was purified to homogeneity by affinity chromatography followed by ion exchange chromatography on mono-Q (Pharmacia) as described hereafter.

Purification of the Soluble IFN-R from Cos7 Cells

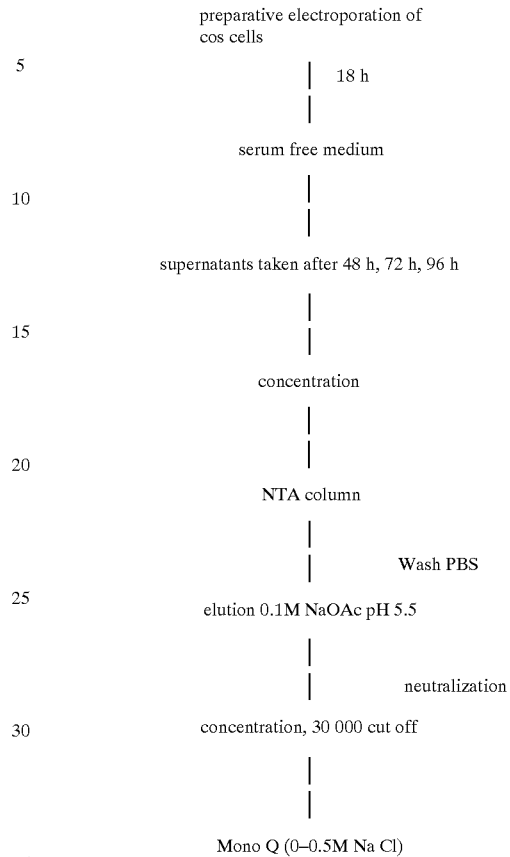

This purification yielded to a 76 kDa protein whose N-terminal sequence corresponds to the predicted receptor sequence with some heterogeneity in the processing of the leader sequence.

Example 2

Production of Monoclonal Antibodies Against the Interferon Type I Receptor

1) Production of the monoclonal antibodies

Mice were immunized by injection of recombinant soluble interferon (r sIFN-R) purified from *E.coli* or from a culture supernatant of Cos7 cells. Initially mice were injected both intraperitoneally and subcutaneously with the purified protein in complete Freund's adjuvant. Subsequently mice were injected once a week intraperitoneally with the purified proteins diluted in buffered saline solution. Ten microgram of recombinant proteins were injected each time.

After the fourth injection, blood was collected and the presence of specific serum antibodies were tested by both ELISA and Western blot against the recombinant receptor. The strongest responders were then boosted with a total of 10 µg of antigen half of which was injected intravenously and half intraperitoneally.

2) Cell fusion

Four days after boosting, spleen cells from the immunized animal were collected and fused to NS1 (mouse) (Balbc) HGPRT$^-$ myeloma cells according to the method described by S. Fazekas et al. (J. Immunol. Methods 35:1–32, 1980). Briefly, $5 \times 10^7$ spleen cells were fused to $3 \times 10^7$ myeloma cells in 1ml of polyethylene glycol solution and distributed in five 96 well plates on a peritoneal macrophage feeder layer in HAT (hypoxanthine, aminoprotein and thymidine) medium. This procedure was repeated 4 times as 20×10⁷ spleen cells were obtained from the immunized mouse. Screening for specific hybridomas was undertaken when large colonies were detectable in culture wells.

For the screening, presence of specific antibodies was determined by a direct ELISA method:

a) ELISA plates were coated overnight at 4° C. with purified *E.coli*-expressed or Cos7 cell-expressed sIFN-R diluted in PBS. Plates coated with BSA were used to detect non specific binding, b) Plates were saturated by incubation with 3% BSA in PBS for 1 hour at 37° C., c) Plates were incubated for 4 hours at room temperature with hybridoma supernatants diluted 1 in 4 with PBS-0.05% Tween 20, d) Bound antibodies were detected by a two step procedure, comprising a first incubation with goat anti-mouse biotinylated immunoglobulin followed by streptavidin-horseradish peroxidase complex (both from Amersham and diluted 1/1000 in PBS-0.05% Tween 20).

Positive antibody secreting hybridomas were passaged in 24 well plates on a spleen cell feeder layer and their reactivity was again checked by ELISA, and Western-blot.

3) Identification of reactivity to the natural interferon type I receptor

The reactivity of the monoclonal antibodies (mAbs) recognizing the recombinant SIFN-R was tested against the natural class I receptor expressed at the surface of Daudi cells, by membrane immunofluorescence. Briefly, 5×10⁵ Daudi cells were incubated in 100 μl of culture supernatant of chosen hybridomas for 30 min at 4° C. The cells were then washed 4 times in RPMI medium containing 1% BSA and further incubated with a diluted FITC labelled goat anti-mouse F(ab')₂ for 30 min at 4° C. The cells were finally analyzed by flow cytometry after washing. One of the 35 tested antibodies produced against the *E.coli* recombinant receptor and 5 of the 6 tested antibodies produced against the COS recombinant receptor were found to recognize the natural receptor on the Daudi cells.

Cloning of these hybridomas was then performed by limiting dilution. The isotype of these mAbs was determined by an ELISA method using isotype specific antibodies. All 6 mAbs were found to be IgGp1 with kappa light chains. A summary of the reactivity of these 6 mAbs is given in Table 1.

Monoclonal antibodies were purified from culture supernatants by protein G chromatography.

TABLE 1

Reactivity of the anti IFN-R monoclonal antibodies

| | Reactivity against the recombinant receptor | | | | Reactivity against* the cellular receptor |
|---|---|---|---|---|---|
| | *E. COLI* | | COS | | |
| | ELISA | Western | ELISA | Western | immunofluorescence |
| 34F10 | + | + | + | + | + |
| 64G12 | + | + | + | + | + |
| 63F6 | | | | | |
| 64G2 | − | − | + | + | + |

TABLE 1-continued

Reactivity of the anti IFN-R monoclonal antibodies

| | Reactivity against the recombinant receptor | | | | Reactivity against* the cellular receptor |
|---|---|---|---|---|---|
| | *E. COLI* | | COS | | |
| | ELISA | Western | ELISA | Western | immunofluorescence |
| 64D10 | | | | | weak |
| 65D8 | | | | | |

*measured on Daudi cells

Example 3
Inhibition of the Binding of Interferon to Human Cell Lines

Inhibition of interferon binding to human cells was assayed as follows. 10⁶ cells were preincubated at 4° C. for 30 min with various dilutions of hybridoma culture supernatants or purified mAbs or with medium alone. $^{125}$I-labelled IFN alpha 8 or alpha 2 was added at the concentration of 100 pM and cells incubated for a further 2 hours at 4° C. These incubations were performed in RPMI medium containing 20 mM HEPES pH 7.4 and 10% foetal calf serum (FCS). The cells were finally washed 4 times with RPMI—1% FCS and counted to determine bound radioactivity.

The mAb secreted by the hybridoma line 64G12 (latter named mAb 64G12) was shown in this assay to inhibit the binding of labelled IFN to the cells in a dose-dependent manner. 50% inhibition of binding to the Daudi cells (Burkitt lymphoma cell line; Klein et al., Cancer Research, 28:1300–1310, 1968) was obtained at a mAb concentration of 0.4 μg/ml. The same inhibition was obtained with K562 cells (chronic myelogenous leukemia, Lozzio and Lozzio, Cell, 45:321–334, 1975) but 50% inhibition was obtained at 11 μg/ml for HL60 cells (Promyelocytic leukemia, Collins S. J. et al., Nature, 270:347–349, 1977) and 60 μg/ml for Ly28 cells (Klein G. et al. Int. J. Cancer, 10:44–57, 1972).

TABLE 2

The inhibition of binding labelled IFN alpha 2 to various cell lines by mAB64G12

| Cell lines | Concentration of mAB which gives 50% inhibition of binding |
|---|---|
| Daudi | 0.4 μg/ml |
| K562 | |
| HL60 | 11 μg/ml |
| Ly28 | 60 μg/ml |

The difference in the mAb concentration at which 50% inhibition of binding of IFN is obtained has been investigated by direct binding of $^{125}$I-labelled mAbs 64G12 and 34F10 to the same cell lines and Scatchard plot analysis of the results. In the concentration range of 0.1 to 1.5 μg/ml, a high affinity binding of the mAb 34F10 (≈10 nM) was seen on all cell lines whereas a high affinity binding of mAB 64G12 was only detected on Daudi and K562 cells (FIG. 1).

Example 4
Inhibition of the Function of Type I Interferon

Functional inhibition of type I interferon by the purified mAb 64Gl2 was demonstrated in an antiviral assay on Daudi cells using either recombinant IFN alpha 2, IFN beta and IFN omega, or purified Namalwa and leucocyte interferons, and in an antiproliferative assay with recombinant IFN alpha 2.

* Antiviral Activity

An antiviral assay on Daudi cells was performed as described (M. Dron and M. G. Tovey, J. Gen. Virol. 64:2641–2647, 1983). Cells ($0.5 \times 10^6$/ml) were incubated for 24 hours in the presence of interferon and antibodies. $10^6$ cells in 1 ml were then infected for 1 hour at 37° C. with Vesicular stomatitis virus (VSV) then washed 3 times, resuspended in culture medium and incubated for 18 hours at 37° C. Cells were then lysed by freeze-thawing and virus replication measured by titration of the supernatants on L929 cells. A dose-dependent inhibition of the antiviral activity of the various subtypes of type I IFN was demonstrated for the purified mAb 64G12.

For the antiviral assay with the Wish cells, cells were incubated for 24 hours with various concentrations of interferons in the presence of the mAbs prior to challenge with VSV. In this assay, the mAb 64G12 was demonstrated to block completely the antiviral activity of Leukocyte IFN (50 U/ml), recombinant IFN alpha 2 (50 U/ml) and interferon from the sera of AIDS patients (50, 75 and 150 U/ml).

* Antiproliferative Activity

For the antiproliferative assay, Daudi cells were seeded at a concentration of $10^5$ cells per ml in a 96 well plate in the presence of interferon and purified inhibitory or control antibody. Cells were then counted after 24, 48 and 72 hours with a Coulter counter and checked for viability by trypan blue exclusion. Purified mAb 64G12 demonstrated a dose-dependent inhibition of the antiproliferative activity of interferon alpha 2.

---

We claim:

1. A monoclonal antibody directed against the human interferon type I receptor (IFN-R) characterized by the following properties:
   it recognizes an epitope on the amino acid sequence 27–427 of SEQ ID NOS: 1 or 2 or of the human INF-R, and,
   it has a neutralizing capacity in vitro against the antiproliferative or antiviral activity of human type I-IFN.

2. The monoclonal antibody directed against the human type I IFN-R according to claim 1, characterized by its capacity to inhibit the binding of a human pathological type I-IFN, to the IFN-R.

3. The monoclonal antibody according to claim 1, which is obtainable from a hybridoma cell prepared by fusion of a myeloma cell with spleen cells from an animal previously immunized with the soluble form of the human IFN-R.

4. The monoclonal antibody according to claim 1, characterized in that it recognizes an epitope on a soluble form of the human cellular IFN-R or of a recombinant IFN-R.

5. The monoclonal antibody according to claim 1, characterized in that it inhibits in vitro the binding of human type I-IFN, to the human cellular IFN-R when it is co-incubated with cells harboring the hu-IFN-R, at a concentration of said antibody equal or inferior to 100 µg/ml.

6. The monoclonal antibody according to claim 1, characterized in that it neutralizes in vitro the antiproliferative activity of the human type I-IFN on Daudi cells at a concentration in a range of 1 to 10 µg/ml.

7. The monoclonal antibody according to claim 1, characterized in that it neutralizes in vitro the antiproliferative activity of the human type I-IFN on LY28 cells at a concentration in a range of 50 to 100 µg/ml.

8. The monoclonal antibody according to claim 1, characterized in that it does not bind to the human receptor of the IFN gamma.

9. Monoclonal antibody according to claim 1, wherein said monoclonal antibody neutralizes in vitro the antiviral activity of the human type I-IFN on Daudi cells at a concentration in a range of 1 to 50 µg/ml for a concentration of type I-IFN in the range of 1 to 1000 units with reference to the international standard MRC69/19.

10. A monoclonal antibody directed against the human interferon type 1 receptor (IFN-R) wherein said monoclonal antibody recognizes the extracellular domain of the human IFN-R of SEQ ID NO: 2 and has a neutralizing capacity in vitro against the biological properties of the human type I-IFN, and wherein said monoclonal antibody is the 64G12 antibody deposited at the ECACC on Feb. 26, 1992 under No. 92022605.

11. A monoclonal antibody, wherein said antibody is a humanized antibody comprising either:

i) the variable regions of the heavy and light chains of the monoclonal antibody according to claim 1 which are grafted on the constant regions of a human antibody, or ii) the complementarity determining regions of the heavy and light chains of the monoclonal antibody of claim 1 which are grafted on the framework of a human antibody.

12. A monoclonal antibody directed against the human interferon class I receptor (IFN-R) wherein said monoclonal antibody recognizes the extracellular domain of the human IFN-R and has a neutralizing capacity against the biological properties of the human type I-IFN, and wherein said monoclonal antibody is the 64G12 antibody deposited at the ECACC on Feb. 26, 1992 under No. 92022605.

13. The monoclonal antibody according to claim 1, characterized in that it is an IgG1 type antibody.

14. A hybridoma cell, characterized in that it produces the monoclonal antibody according to claim 1.

15. A composition having antagonist properties to the type I-IFN, characterized in that it comprises the monoclonal antibody according to claim 1.

16. A pharmaceutical composition, characterized in that it comprises the monoclonal antibody according to claim 1, together with an appropriate pharmaceutical vehicle.

17. A humanized antibody that specifically binds to the human interferon type I receptor.

18. A human monoclonal antibody that specifically binds to the extracellular domain of the human interferon type I receptor.

19. The monoclonal antibody according to claim 5, wherein said antibody concentration is equal or inferior to 50 $\mu$g/ml.

20. The monoclonal antibody according to claim 5, wherein said antibody concentration is equal or inferior to 20 $\mu$g/ml.

21. A monoclonal antibody according to claim 5, wherein said antibody concentration is in the range of about 0.5 to 2 $\mu$g/ml.

22. A method of treatment or prophylaxis of allograft rejection or autoimmune disease associated with abnormal production of human interferon type-I, comprising administering to a patient in need thereof an effective therapeutic or prophylactic amount of the monoclonal antibody according to claim 1.

* * * * *

UNITED STATES PATENT AND TRADEMARK OFFICE
CERTIFICATE OF CORRECTION

PATENT NO. : 5,919,453
DATED : July 6, 1999
INVENTOR(S) : BENOIT, et al..

It is certified that error appears in the above-identified patent and that said Letters Patent is hereby corrected as shown below:

Claim 1, line 5, and change "human INF-R"

Should read -- human IFN-R --

Signed and Sealed this

Twenty-seventh Day of March, 2001

Attest:

NICHOLAS P. GODICI

Attesting Officer

Acting Director of the United States Patent and Trademark Office

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 1343 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 27..1334

(xi) SEQUENCE DESCRIPTION: SEQ ID NO: 1:

```
CTGCAGGGAT CTGCGGCGGC TCCCAG ATG ATG GTC GTC CTC CTG GGC GCG ACG        53
                             Met Met Val Val Leu Leu Gly Ala Thr
                              1               5

ACC CTA GTG CTC GTC GCC GTG GGC CCA TGG GTG TTG TCC GCA GCC GCA        101
Thr Leu Val Leu Val Ala Val Gly Pro Trp Val Leu Ser Ala Ala Ala
 10              15                  20                  25

GGT GGA AAA AAT CTA AAA TCT CCT CAA AAA GTA GAG GTC GAC ATC ATA        149
Gly Gly Lys Asn Leu Lys Ser Pro Gln Lys Val Glu Val Asp Ile Ile
                 30                  35                  40

GAT GAC AAC TTT ATC CTG AGG TGG AAC AGG AGC GAT GAG TCT GTC GGG        197
Asp Asp Asn Phe Ile Leu Arg Trp Asn Arg Ser Asp Glu Ser Val Gly
             45                  50                  55

AAT GTG ACT TTT TCA TTC GAT TAT CAA AAA ACT GGG ATG GAT AAT TGG        245
Asn Val Thr Phe Ser Phe Asp Tyr Gln Lys Thr Gly Met Asp Asn Trp
         60                  65                  70

ATA AAA TTG TCT GGG TGT CAG AAT ATT ACT AGT ACC AAA TGC AAC TTT        293
Ile Lys Leu Ser Gly Cys Gln Asn Ile Thr Ser Thr Lys Cys Asn Phe
 75                  80                  85

TCT TCA CTC AAG CTG AAT GTT TAT GAA GAA ATT AAA TTG CGT ATA AGA        341
Ser Ser Leu Lys Leu Asn Val Tyr Glu Glu Ile Lys Leu Arg Ile Arg
 90                  95                 100                 105

GCA GAA AAA GAA AAC ACT TCT TCA TGG TAT GAG GTT GAC TCA TTT ACA        389
Ala Glu Lys Glu Asn Thr Ser Ser Trp Tyr Glu Val Asp Ser Phe Thr
                110                 115                 120

CCA TTT CGC AAA GCT CAG ATT GGT CCT CCA GAA GTA CAT TTA GAA GCT        437
Pro Phe Arg Lys Ala Gln Ile Gly Pro Pro Glu Val His Leu Glu Ala
            125                 130                 135
```

```
GAA GAT AAG GCA ATA GTG ATA CAC ATC TCT CCT GGA ACA AAA GAT AGT        485
Glu Asp Lys Ala Ile Val Ile His Ile Ser Pro Gly Thr Lys Asp Ser
        140                 145                 150

GTT ATG TGG GCT TTG GAT GGT TTA AGC TTT ACA TAT AGC TTA CTT ATC        533
Val Met Trp Ala Leu Asp Gly Leu Ser Phe Thr Tyr Ser Leu Leu Ile
155                 160                 165

TGG AAA AAC TCT TCA GGT GTA GAA GAA AGG ATT GAA AAT ATT TAT TCC        581
Trp Lys Asn Ser Ser Gly Val Glu Glu Arg Ile Glu Asn Ile Tyr Ser
170                 175                 180                 185

AGA CAT AAA ATT TAT AAA CTC TCA CCA GAG ACT ACT TAT TGT CTA AAA        629
Arg His Lys Ile Tyr Lys Leu Ser Pro Glu Thr Thr Tyr Cys Leu Lys
                    190                 195                 200

GTT AAA GCA GCA CTA CTT ACG TCA TGG AAA ATT GGT GTC TAT AGT CCA        677
Val Lys Ala Ala Leu Leu Thr Ser Trp Lys Ile Gly Val Tyr Ser Pro
        205                 210                 215

GTA CAT TGT ATA AAG ACC ACA GTT GAA AAT GAA CTA CCT CCA CCA GAA        725
Val His Cys Ile Lys Thr Thr Val Glu Asn Glu Leu Pro Pro Pro Glu
        220                 225                 230

AAT ATA GAA GTC AGT GTC CAA AAT CAG AAC TAT GTT CTT AAA TGG GAT        773
Asn Ile Glu Val Ser Val Gln Asn Gln Asn Tyr Val Leu Lys Trp Asp
235                 240                 245

TAT ACA TAT GCA AAC ATG ACC TTT CAA GTT CAG TGG CTC CAC GCC TTT        821
Tyr Thr Tyr Ala Asn Met Thr Phe Gln Val Gln Trp Leu His Ala Phe
250                 255                 260                 265

TTA AAA AGG AAT CCT GGA AAC CAT TTG TAT AAA TGG AAA CAA ATA CCT        869
Leu Lys Arg Asn Pro Gly Asn His Leu Tyr Lys Trp Lys Gln Ile Pro
                    270                 275                 280

GAC TGT GAA AAT GTC AAA ACT ACC CAG TGT GTC TTT CCT CAA AAC GTT        917
Asp Cys Glu Asn Val Lys Thr Thr Gln Cys Val Phe Pro Gln Asn Val
        285                 290                 295

TTC CAA AAA GGA ATT TAC CTT CTC CGC GTA CAA GCA TCT GAT GGA AAT        965
Phe Gln Lys Gly Ile Tyr Leu Leu Arg Val Gln Ala Ser Asp Gly Asn
        300                 305                 310

AAC ACA TCT TTT TGG TCT GAA GAG ATA AAG TTT GAT ACT GAA ATA CAA       1013
Asn Thr Ser Phe Trp Ser Glu Glu Ile Lys Phe Asp Thr Glu Ile Gln
        315                 320                 325

GCT TTC CTA CTT CCT CCA GTC TTT AAC ATT AGA TCC CTT AGT GAT TCA       1061
Ala Phe Leu Leu Pro Pro Val Phe Asn Ile Arg Ser Leu Ser Asp Ser
330                 335                 340                 345

TTC CAT ATC TAT ATC GGT GCT CCA AAA CAG TCT GGA AAC ACG CCT GTG       1109
Phe His Ile Tyr Ile Gly Ala Pro Lys Gln Ser Gly Asn Thr Pro Val
                    350                 355                 360

ATC CAG GAT TAT CCA CTG ATT TAT GAA ATT ATT TTT TGG GAA AAC ACT       1157
Ile Gln Asp Tyr Pro Leu Ile Tyr Glu Ile Ile Phe Trp Glu Asn Thr
            365                 370                 375

TCA AAT GCT GAG AGA AAA ATT ATC GAG AAA AAA ACT GAT GTT ACA GTT       1205
Ser Asn Ala Glu Arg Lys Ile Ile Glu Lys Lys Thr Asp Val Thr Val
        380                 385                 390

CCT AAT TTG AAA CCA CTG ACT GTA TAT TGT GTG AAA GCC AGA GCA CAC       1253
Pro Asn Leu Lys Pro Leu Thr Val Tyr Cys Val Lys Ala Arg Ala His
        395                 400                 405

ACC ATG GAT GAA AAG CTG AAT AAA AGC AGT GTT TTT AGT GAC GCT GTA       1301
Thr Met Asp Glu Lys Leu Asn Lys Ser Ser Val Phe Ser Asp Ala Val
410                 415                 420                 425

TGT GAG AAA ACA AAA CCA GGA AAT ACC TCT AAA TGAGGTACC                 1343
Cys Glu Lys Thr Lys Pro Gly Asn Thr Ser Lys
                    430                 435
```

(2) INFORMATION FOR SEQ ID NO: 2:

(i) SEQUENCE CHARACTERISTICS:

(A) LENGTH: 436 amino acids
(B) TYPE: amino acid
(D) TOPOLOGY: linear (ii) MOLECULE TYPE: protein (xi) SEQUENCE DESCRIPTION: SEQ ID NO: 2:

```
Met Met Val Val Leu Leu Gly Ala Thr Thr Leu Val Leu Val Ala Val
 1               5                  10                  15

Gly Pro Trp Val Leu Ser Ala Ala Gly Gly Lys Asn Leu Lys Ser
                20                  25                  30

Pro Gln Lys Val Glu Val Asp Ile Ile Asp Asp Asn Phe Ile Leu Arg
            35                  40                  45

Trp Asn Arg Ser Asp Glu Ser Val Gly Asn Val Thr Phe Ser Phe Asp
        50                  55                  60

Tyr Gln Lys Thr Gly Met Asp Asn Trp Ile Lys Leu Ser Gly Cys Gln
 65                  70                  75                  80

Asn Ile Thr Ser Thr Lys Cys Asn Phe Ser Ser Leu Lys Leu Asn Val
                85                  90                  95

Tyr Glu Glu Ile Lys Leu Arg Ile Arg Ala Lys Glu Asn Thr Ser
                100                 105                 110

Ser Trp Tyr Glu Val Asp Ser Phe Thr Pro Phe Arg Lys Ala Gln Ile
            115                 120                 125

Gly Pro Pro Glu Val His Leu Glu Ala Glu Asp Lys Ala Ile Val Ile
        130                 135                 140

His Ile Ser Pro Gly Thr Lys Asp Ser Val Met Trp Ala Leu Asp Gly
145                 150                 155                 160

Leu Ser Phe Thr Tyr Ser Leu Leu Ile Trp Lys Asn Ser Ser Gly Val
                165                 170                 175

Glu Glu Arg Ile Glu Asn Ile Tyr Ser Arg His Lys Ile Tyr Lys Leu
            180                 185                 190

Ser Pro Glu Thr Thr Tyr Cys Leu Lys Val Lys Ala Ala Leu Leu Thr
        195                 200                 205

Ser Trp Lys Ile Gly Val Tyr Ser Pro Val His Cys Ile Lys Thr Thr
210                 215                 220

Val Glu Asn Glu Leu Pro Pro Pro Glu Asn Ile Glu Val Ser Val Gln
225                 230                 235                 240

Asn Gln Asn Tyr Val Leu Lys Trp Asp Tyr Thr Tyr Ala Asn Met Thr
                245                 250                 255

Phe Gln Val Gln Trp Leu His Ala Phe Leu Lys Arg Asn Pro Gly Asn
            260                 265                 270

His Leu Tyr Lys Trp Lys Gln Ile Pro Asp Cys Glu Asn Val Lys Thr
        275                 280                 285

Thr Gln Cys Val Phe Pro Gln Asn Val Phe Gln Lys Gly Ile Tyr Leu
290                 295                 300

Leu Arg Val Gln Ala Ser Asp Gly Asn Asn Thr Ser Phe Trp Ser Glu
305                 310                 315                 320

Glu Ile Lys Phe Asp Thr Glu Ile Gln Ala Phe Leu Leu Pro Pro Val
                325                 330                 335

Phe Asn Ile Arg Ser Leu Ser Asp Ser Phe His Ile Tyr Ile Gly Ala
            340                 345                 350

Pro Lys Gln Ser Gly Asn Thr Pro Val Ile Gln Asp Tyr Pro Leu Ile
        355                 360                 365

Tyr Glu Ile Ile Phe Trp Glu Asn Thr Ser Asn Ala Glu Arg Lys Ile
370                 375                 380
```

```
Ile Glu Lys Lys Thr Asp Val Thr Val Pro Asn Leu Lys Pro Leu Thr
385                 390                 395                 400

Val Tyr Cys Val Lys Ala Arg Ala His Thr Met Asp Glu Lys Leu Asn
                405                 410                 415

Lys Ser Ser Val Phe Ser Asp Ala Val Cys Glu Lys Thr Lys Pro Gly
                420                 425                 430

Asn Thr Ser Lys
            435
```

(2) INFORMATION FOR SEQ ID NO: 3:

(i) SEQUENCE CHARACTERISTICS:
        (A) LENGTH: 1755 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 27..1697

(xi) SEQUENCE DESCRIPTION: SEQ ID NO: 3:

```
CTGCAGGGAT CTGCGGCGGC TCCCAG ATG ATG GTC GTC CTC CTG GGC GCG ACG        53
                             Met Met Val Val Leu Leu Gly Ala Thr
                              1               5

ACC CTA GTG CTC GTC GCC GTG GGC CCA TGG GTG TTG TCC GCA GCC GCA        101
Thr Leu Val Leu Val Ala Val Gly Pro Trp Val Leu Ser Ala Ala Ala
 10              15                  20                  25

GGT GGA AAA AAT CTA AAA TCT CCT CAA AAA GTA GAG GTC GAC ATC ATA        149
Gly Gly Lys Asn Leu Lys Ser Pro Gln Lys Val Glu Val Asp Ile Ile
                 30                  35                  40

GAT GAC AAC TTT ATC CTG AGG TGG AAC AGG AGC GAT GAG TCT GTC GGG        197
Asp Asp Asn Phe Ile Leu Arg Trp Asn Arg Ser Asp Glu Ser Val Gly
             45                  50                  55

AAT GTG ACT TTT TCA TTC GAT TAT CAA AAA ACT GGG ATG GAT AAT TGG        245
Asn Val Thr Phe Ser Phe Asp Tyr Gln Lys Thr Gly Met Asp Asn Trp
         60                  65                  70

ATA AAA TTG TCT GGG TGT CAG AAT ATT ACT AGT ACC AAA TGC AAC TTT        293
Ile Lys Leu Ser Gly Cys Gln Asn Ile Thr Ser Thr Lys Cys Asn Phe
     75                  80                  85

TCT TCA CTC AAG CTG AAT GTT TAT GAA GAA ATT AAA TTG CGT ATA AGA        341
Ser Ser Leu Lys Leu Asn Val Tyr Glu Glu Ile Lys Leu Arg Ile Arg
 90                  95                 100                 105

GCA GAA AAA GAA AAC ACT TCT TCA TGG TAT GAG GTT GAC TCA TTT ACA        389
Ala Glu Lys Glu Asn Thr Ser Ser Trp Tyr Glu Val Asp Ser Phe Thr
                110                 115                 120

CCA TTT CGC AAA GCT CAG ATT GGT CCT CCA GAA GTA CAT TTA GAA GCT        437
Pro Phe Arg Lys Ala Gln Ile Gly Pro Pro Glu Val His Leu Glu Ala
            125                 130                 135

GAA GAT AAG GCA ATA GTG ATA CAC ATC TCT CCT GGA ACA AAA GAT AGT        485
Glu Asp Lys Ala Ile Val Ile His Ile Ser Pro Gly Thr Lys Asp Ser
        140                 145                 150

GTT ATG TGG GCT TTG GAT GGT TTA AGC TTT ACA TAT AGC TTA CTT ATC        533
Val Met Trp Ala Leu Asp Gly Leu Ser Phe Thr Tyr Ser Leu Leu Ile
    155                 160                 165

TGG AAA AAC TCT TCA GGT GTA GAA GAA AGG ATT GAA AAT ATT TAT TCC        581
Trp Lys Asn Ser Ser Gly Val Glu Glu Arg Ile Glu Asn Ile Tyr Ser
170                 175                 180                 185

AGA CAT AAA ATT TAT AAA CTC TCA CCA GAG ACT ACT TAT TGT CTA AAA        629
Arg His Lys Ile Tyr Lys Leu Ser Pro Glu Thr Thr Tyr Cys Leu Lys
                190                 195                 200
```

```
GTT AAA GCA GCA CTA CTT ACG TCA TGG AAA ATT GGT GTC TAT AGT CCA    677
Val Lys Ala Ala Leu Leu Thr Ser Trp Lys Ile Gly Val Tyr Ser Pro
        205                 210                 215

GTA CAT TGT ATA AAG ACC ACA GTT GAA AAT GAA CTA CCT CCA CCA GAA    725
Val His Cys Ile Lys Thr Thr Val Glu Asn Glu Leu Pro Pro Pro Glu
        220                 225                 230

AAT ATA GAA GTC AGT GTC CAA AAT CAG AAC TAT GTT CTT AAA TGG GAT    773
Asn Ile Glu Val Ser Val Gln Asn Gln Asn Tyr Val Leu Lys Trp Asp
235                 240                 245

TAT ACA TAT GCA AAC ATG ACC TTT CAA GTT CAG TGG CTC CAC GCC TTT    821
Tyr Thr Tyr Ala Asn Met Thr Phe Gln Val Gln Trp Leu His Ala Phe
250                 255                 260                 265

TTA AAA AGG AAT CCT GGA AAC CAT TTG TAT AAA TGG AAA CAA ATA CCT    869
Leu Lys Arg Asn Pro Gly Asn His Leu Tyr Lys Trp Lys Gln Ile Pro
            270                 275                 280

GAC TGT GAA AAT GTC AAA ACT ACC CAG TGT GTC TTT CCT CAA AAC GTT    917
Asp Cys Glu Asn Val Lys Thr Thr Gln Cys Val Phe Pro Gln Asn Val
                285                 290                 295

TTC CAA AAA GGA ATT TAC CTT CTC CGC GTA CAA GCA TCT GAT GGA AAT    965
Phe Gln Lys Gly Ile Tyr Leu Leu Arg Val Gln Ala Ser Asp Gly Asn
            300                 305                 310

AAC ACA TCT TTT TGG TCT GAA GAG ATA AAG TTT GAT ACT GAA ATA CAA   1013
Asn Thr Ser Phe Trp Ser Glu Glu Ile Lys Phe Asp Thr Glu Ile Gln
        315                 320                 325

GCT TTC CTA CTT CCT CCA GTC TTT AAC ATT AGA TCC TTA AGT GAT TCA   1061
Ala Phe Leu Leu Pro Pro Val Phe Asn Ile Arg Ser Leu Ser Asp Ser
330                 335                 340                 345

TTC CAT ATC TAT ATC GGT GCT CCA AAA CAG TCT GGA AAC ACG CCT GTG   1109
Phe His Ile Tyr Ile Gly Ala Pro Lys Gln Ser Gly Asn Thr Pro Val
                350                 355                 360

ATC CAG GAT TAT CCA CTG ATT TAT GAA ATT ATT TTT TGG GAA AAC ACT   1157
Ile Gln Asp Tyr Pro Leu Ile Tyr Glu Ile Ile Phe Trp Glu Asn Thr
            365                 370                 375

TCA AAT GCT GAG AGA AAA ATT ATC GAG AAA AAA ACT GAT GTT ACA GTT   1205
Ser Asn Ala Glu Arg Lys Ile Ile Glu Lys Lys Thr Asp Val Thr Val
        380                 385                 390

CCT AAT TTG AAA CCA CTG ACT GTA TAT TGT GTG AAA GCC AGA GCA CAC   1253
Pro Asn Leu Lys Pro Leu Thr Val Tyr Cys Val Lys Ala Arg Ala His
395                 400                 405

ACC ATG GAT GAA AAG CTG AAT AAA AGC AGT GTT TTT AGT GAC GCT GTA   1301
Thr Met Asp Glu Lys Leu Asn Lys Ser Ser Val Phe Ser Asp Ala Val
410                 415                 420                 425

TGT GAG AAA ACA AAA CCA GGA AAT ACC TCT AAA ATT TGG CTT ATA GTT   1349
Cys Glu Lys Thr Lys Pro Gly Asn Thr Ser Lys Ile Trp Leu Ile Val
                430                 435                 440

GGA ATT TGT ATT GCA TTA TTT GCT CTC CCG TTT GTC ATT TAT GCT GCG   1397
Gly Ile Cys Ile Ala Leu Phe Ala Leu Pro Phe Val Ile Tyr Ala Ala
            445                 450                 455

AAA GTC TTC TTG AGA TGC ATC AAT TAT GTC TTC TTT CCA TCA CTT AAA   1445
Lys Val Phe Leu Arg Cys Ile Asn Tyr Val Phe Phe Pro Ser Leu Lys
        460                 465                 470

CCT TCT TCC AGT ATA GAT GAG TAT TTC TCT GAA CAG CCA TTG AAG AAT   1493
Pro Ser Ser Ser Ile Asp Glu Tyr Phe Ser Glu Gln Pro Leu Lys Asn
475                 480                 485

CTT CTG CTT TCA ACT TCT GAG GAA CAA ATC GAA AAA TGT TTC ATA ATT   1541
Leu Leu Leu Ser Thr Ser Glu Glu Gln Ile Glu Lys Cys Phe Ile Ile
490                 495                 500                 505

GAA AAT ATA AGC ACA ATT GCT ACA GTA GAA GAA ACT AAT CAA ACT GAT   1589
Glu Asn Ile Ser Thr Ile Ala Thr Val Glu Glu Thr Asn Gln Thr Asp
                510                 515                 520
```

```
GAA GAT CAT AAA AAA TAC AGT TCC CAA ACT AGC CAA GAT TCA GGA AAT        1637
Glu Asp His Lys Lys Tyr Ser Ser Gln Thr Ser Gln Asp Ser Gly Asn
            525                 530                 535

TAT TCT AAT GAA GAT GAA AGC GAA AGT AAA ACA AGT GAA GAA CTA CAG        1685
Tyr Ser Asn Glu Asp Glu Ser Glu Ser Lys Thr Ser Glu Glu Leu Gln
                540                 545                 550

CAG GAC TTT GTA TGACCAGAAA TGAACTGTGT CAAGTATAAG GTTTTTCAGC            1737
Gln Asp Phe Val
        555

AGGAGTTACA CTGGTACC                                                    1755
```

(2) INFORMATION FOR SEQ ID NO: 4:

(i) SEQUENCE CHARACTERISTICS:
        (A) LENGTH: 557 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Met Val Val Leu Leu Gly Ala Thr Thr Leu Val Leu Val Ala Val
 1               5                  10                  15

Gly Pro Trp Val Leu Ser Ala Ala Gly Gly Lys Asn Leu Lys Ser
                20                  25                  30

Pro Gln Lys Val Glu Val Asp Ile Ile Asp Asn Phe Ile Leu Arg
            35                  40                  45

Trp Asn Arg Ser Asp Glu Ser Val Gly Asn Val Thr Phe Ser Phe Asp
 50                  55                  60

Tyr Gln Lys Thr Gly Met Asp Asn Trp Ile Lys Leu Ser Gly Cys Gln
 65                  70                  75                  80

Asn Ile Thr Ser Thr Lys Cys Asn Phe Ser Ser Leu Lys Leu Asn Val
                85                  90                  95

Tyr Glu Glu Ile Lys Leu Arg Ile Arg Ala Glu Lys Glu Asn Thr Ser
                100                 105                 110

Ser Trp Tyr Glu Val Asp Ser Phe Thr Pro Phe Arg Lys Ala Gln Ile
            115                 120                 125

Gly Pro Pro Glu Val His Leu Glu Ala Glu Asp Lys Ala Ile Val Ile
130                 135                 140

His Ile Ser Pro Gly Thr Lys Asp Ser Val Met Trp Ala Leu Asp Gly
145                 150                 155                 160

Leu Ser Phe Thr Tyr Ser Leu Leu Ile Trp Lys Asn Ser Ser Gly Val
                165                 170                 175

Glu Glu Arg Ile Glu Asn Ile Tyr Ser Arg His Lys Ile Tyr Lys Leu
            180                 185                 190

Ser Pro Glu Thr Thr Tyr Cys Leu Lys Val Lys Ala Ala Leu Leu Thr
            195                 200                 205

Ser Trp Lys Ile Gly Val Tyr Ser Pro Val His Cys Ile Lys Thr Thr
210                 215                 220

Val Glu Asn Glu Leu Pro Pro Pro Glu Asn Ile Glu Val Ser Val Gln
225                 230                 235                 240

Asn Gln Asn Tyr Val Leu Lys Trp Asp Tyr Thr Tyr Ala Asn Met Thr
                245                 250                 255

Phe Gln Val Gln Trp Leu His Ala Phe Leu Lys Arg Asn Pro Gly Asn
            260                 265                 270

His Leu Tyr Lys Trp Lys Gln Ile Pro Asp Cys Glu Asn Val Lys Thr
            275                 280                 285
```

```
Thr Gln Cys Val Phe Pro Gln Asn Val Phe Gln Lys Gly Ile Tyr Leu
    290                 295                 300

Leu Arg Val Gln Ala Ser Asp Gly Asn Asn Thr Ser Phe Trp Ser Glu
305                 310                 315                 320

Glu Ile Lys Phe Asp Thr Glu Ile Gln Ala Phe Leu Leu Pro Pro Val
                325                 330                 335

Phe Asn Ile Arg Ser Leu Ser Asp Ser Phe His Ile Tyr Ile Gly Ala
            340                 345                 350

Pro Lys Gln Ser Gly Asn Thr Pro Val Ile Gln Asp Tyr Pro Leu Ile
        355                 360                 365

Tyr Glu Ile Ile Phe Trp Glu Asn Thr Ser Asn Ala Glu Arg Lys Ile
    370                 375                 380

Ile Glu Lys Lys Thr Asp Val Thr Val Pro Asn Leu Lys Pro Leu Thr
385                 390                 395                 400

Val Tyr Cys Val Lys Ala Arg Ala His Thr Met Asp Glu Lys Leu Asn
                405                 410                 415

Lys Ser Ser Val Phe Ser Asp Ala Val Cys Glu Lys Thr Lys Pro Gly
            420                 425                 430

Asn Thr Ser Lys Ile Trp Leu Ile Val Gly Ile Cys Ile Ala Leu Phe
        435                 440                 445

Ala Leu Pro Phe Val Ile Tyr Ala Ala Lys Val Phe Leu Arg Cys Ile
    450                 455                 460

Asn Tyr Val Phe Phe Pro Ser Leu Lys Pro Ser Ser Ser Ile Asp Glu
465                 470                 475                 480

Tyr Phe Ser Glu Gln Pro Leu Lys Asn Leu Leu Leu Ser Thr Ser Glu
                485                 490                 495

Glu Gln Ile Glu Lys Cys Phe Ile Ile Glu Asn Ile Ser Thr Ile Ala
            500                 505                 510

Thr Val Glu Glu Thr Asn Gln Thr Asp Glu Asp His Lys Lys Tyr Ser
        515                 520                 525

Ser Gln Thr Ser Gln Asp Ser Gly Asn Tyr Ser Asn Glu Asp Glu Ser
    530                 535                 540

Glu Ser Lys Thr Ser Glu Glu Leu Gln Gln Asp Phe Val
545                 550                 555
```